(12) United States Patent
Nemoto et al.

(10) Patent No.: US 7,455,659 B2
(45) Date of Patent: Nov. 25, 2008

(54) LIQUID INJECTION SYSTEM WITH PISTON ADAPTER OPERABLE INTO AND OUT OF ENGAGEMENT WITH PISTON OF RODLESS SYRINGE

(75) Inventors: Shigeru Nemoto, Tokyo (JP); Nobuhisa Tano, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 846 days.

(21) Appl. No.: 10/849,421

(22) Filed: May 19, 2004

(65) Prior Publication Data

US 2004/0249344 A1 Dec. 9, 2004

(30) Foreign Application Priority Data

Jun. 6, 2003 (JP) ............................ 2003-162011

(51) Int. Cl.
*A61M 1/00* (2006.01)
(52) U.S. Cl. ..................................... 604/152
(58) Field of Classification Search ............... 604/131, 604/151, 152, 154, 218, 221, 224, 187, 220, 604/228
See application file for complete search history.

(56) References Cited

U.S. PATENT DOCUMENTS

| | | | |
|---|---|---|---|
| 6,752,789 B2 * | 6/2004 | Duchon et al. ............. | 604/228 |
| 2001/0023336 A1 | 9/2001 | Nolan, Jr. et al. | |
| 2002/0029017 A1 | 3/2002 | Neer et al. | |
| 2002/0115933 A1 | 8/2002 | Duchon et al. | |
| 2002/0169415 A1 | 11/2002 | Staats et al. | |

FOREIGN PATENT DOCUMENTS

| | | |
|---|---|---|
| EP | 0 346 950 A2 | 12/1989 |
| EP | 0 514 907 A1 | 11/1992 |
| EP | 1 195 172 A2 | 4/2002 |
| FR | 2.091.684 | 1/1972 |
| JP | 2001-011096 | 1/2002 |
| JP | 2002-102343 | 4/2002 |
| WO | WO 02/04049 A1 | 1/2002 |
| WO | WO 02/07812 A2 | 1/2002 |

* cited by examiner

*Primary Examiner*—Nicholas D. Lucchesi
*Assistant Examiner*—Theodore J Stigell
(74) *Attorney, Agent, or Firm*—Knobb Martens Olson & Bear LLP

(57) ABSTRACT

A piston adapter has a flange holding mechanism mounted on a distal end thereof for releasably holding a piston flange of a piston of a rodless syringe, a manual operating member disposed on a tip end of the piston adapter for being manually operated, and an interlink mechanism for releasing the flange holding mechanism from the piston flange in conjunction with manual operation of the manual operating member. After the piston adapter is mounted on the piston of the rodless syringe and inserted into the cylinder thereof, the flange holding mechanism can be released from the piston in the cylinder by manually operating the manual operating member near the tip end of the piston adapter which is exposed from the cylinder. Even when the piston adapter that is mounted on the piston of the rodless syringe is pressed into the cylinder, the piston adapter can easily be removed from the rodless syringe.

5 Claims, 11 Drawing Sheets

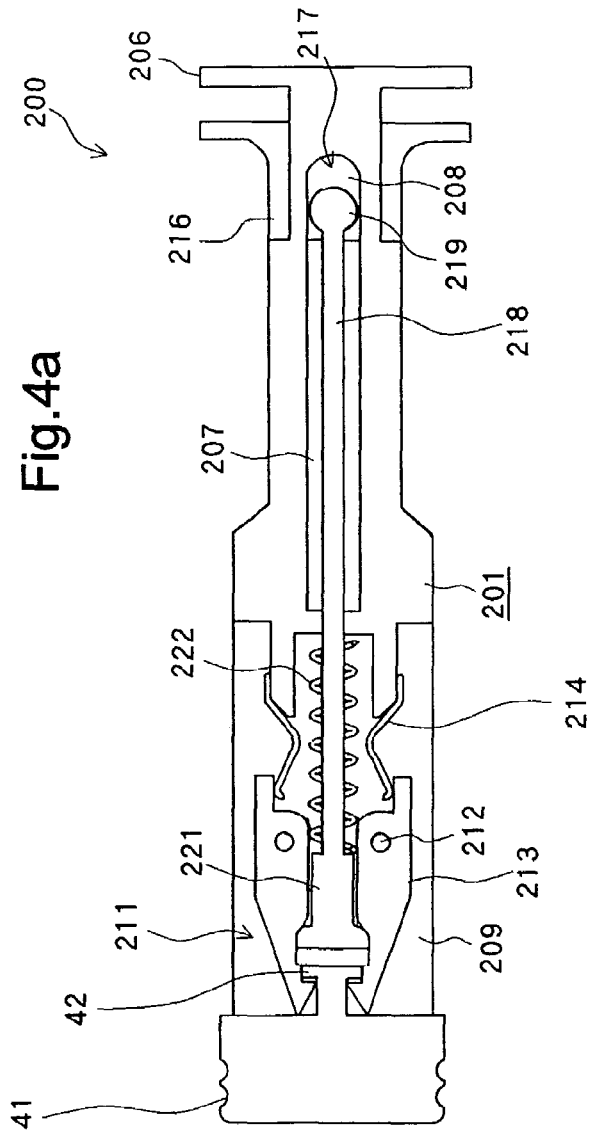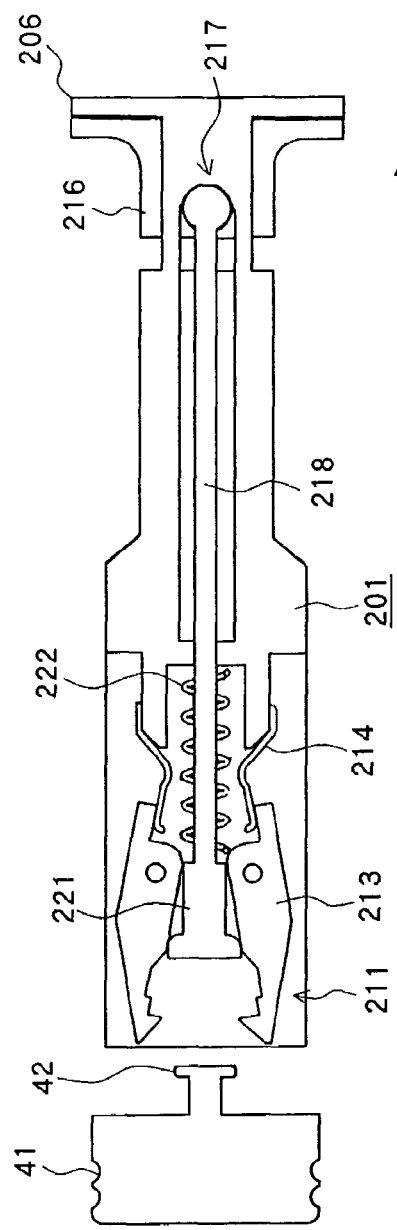

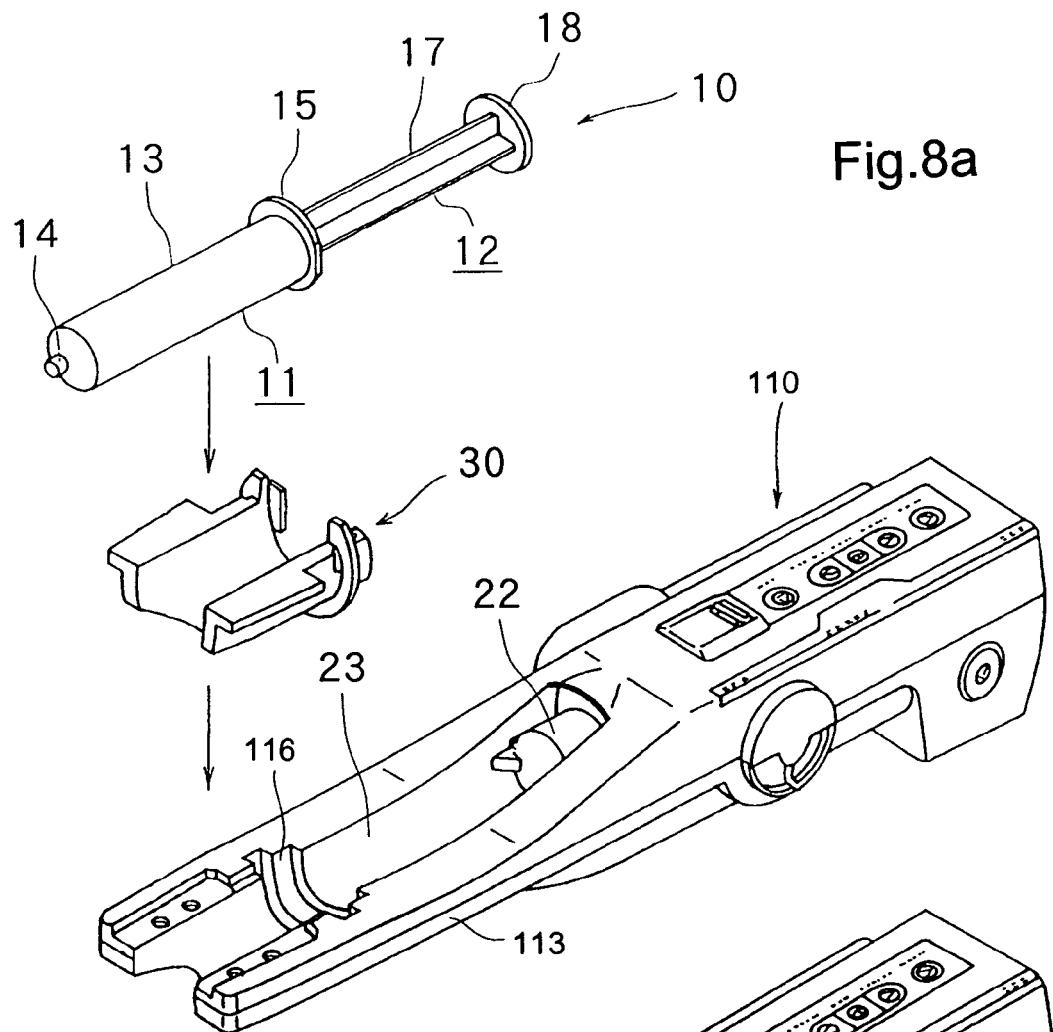
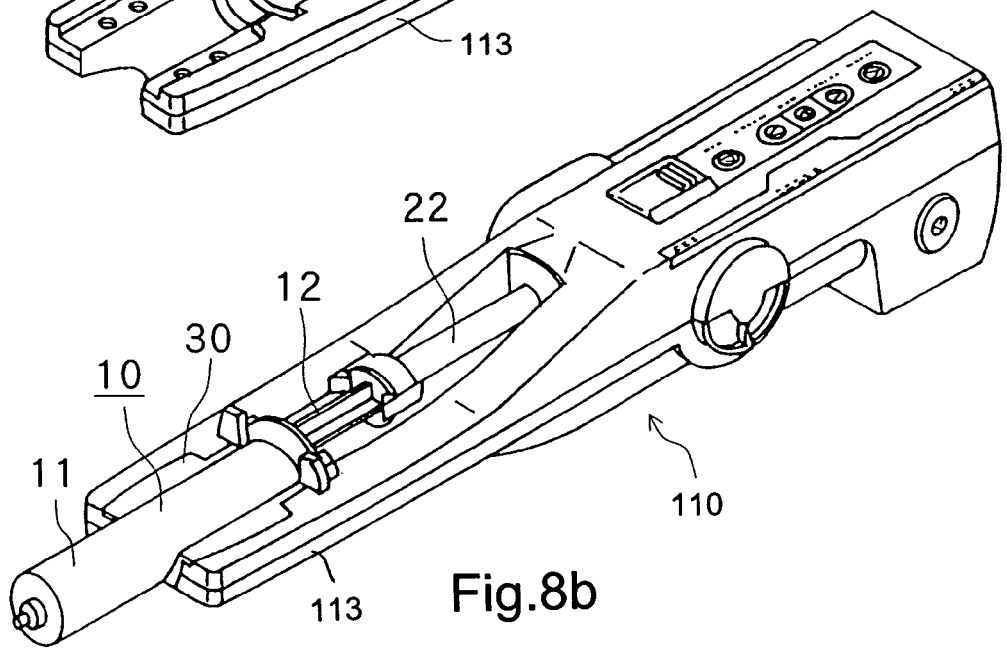

LIQUID INJECTION SYSTEM WITH PISTON ADAPTER OPERABLE INTO AND OUT OF ENGAGEMENT WITH PISTON OF RODLESS SYRINGE

BACKGROUND OF THE INVENTION

1. Field of the Invention

The present invention relates to a liquid injection system which includes a liquid injector for injecting a liquid from a normal syringe into a patient, and more particularly to a liquid injection system which allows a rodless syringe to be mounted on a liquid injector by a piston adapter.

2. Description of the Related Art

Presently available imaging diagnostic apparatus for capturing fluoroscopic images of patients include CT (Computed Tomography) scanners, MRI (Magnetic Resonance Imaging) apparatus, PET (Positron Emission Tomography) apparatus, ultrasonic diagnostic apparatus, angiography apparatus, and MRA (MR Angiography) apparatus.

When such an imaging diagnostic apparatus is used to capture a fluoroscopic image of a patient, it is occasionally practiced to inject a liquid such as a contrast medium or a saline solution into the patient. There has been put to practical use a liquid injector for automatically injecting a liquid into a patient. A conventional liquid injector will be described below with reference to FIGS. 1 through 3 of the accompanying drawings.

As shown in FIG. 1, normal syringe 10 serving as a liquid syringe comprises cylinder 11 and piston 12 slidably inserted in cylinder 11. Cylinder 11 has slender cylindrical cylinder casing 13. Cylinder casing 13 is closed at a distal end thereof and has central hollow conduit 14 disposed on the closed distal end. Cylinder casing 13 also has cylinder flange 15 disposed on the outer circumferential edge of an opposite open end thereof.

Piston 12 has slender piston rod 17 having piston flange 18 disposed on the outer circumferential edge of an end thereof. Piston head 19 made of an elastic material such as rubber or synthetic resin is mounted on a distal end of piston rod 17. Piston rod 17 is slidably inserted in cylinder 11.

Liquid injector 20 comprises single injection head 21 and two piston actuating mechanisms 22. Single injection head 21 has two recesses 23 for individually holding cylinders 11 of two normal syringes 10. Two piston actuating mechanisms 22 are disposed respectively behind two recesses 23 for holding and moving respective pistons 12 of normal syringes 10.

More specifically, as shown in FIG. 2, piston actuating mechanism 22 has slide rod 25 which is slidable longitudinally and piston presser 26 integrally formed with a front end of slide rod 25 for abutting against the rear surface of piston 12 from behind.

Piston presser 26 has a pair of engaging teeth 27 that are openable and closable, i.e., movable toward and away from each other, horizontally. When engaging teeth 27 are moved toward each other while piston presser 26 is in abutment against piston 12, they engage respective left and right edge portions of the front surface of piston flange 15.

A plurality of types of normal syringes 10 are available for use on liquid injector 20. Normal syringes 10 of those types are made up of components in different sizes and shapes. The liquid injection system which uses liquid injector 20 has as many cylinder adapters 30 provided in readiness for use as the number of different types of normal syringes 10 except for normal syringes 10 of the maximum size.

Cylinder adapters 30 have an outer shape identical to the outer shape of cylinder 11 of normal syringe 10 of the maximum size, and have respective adapter flanges 31 disposed on the outer circumferential edge of an end thereof. Adapter flanges 31 are of the same shape as cylinder flange 15 of normal syringe 10 of the maximum size.

Cylinders 11 of normal syringes 10 of the maximum size or cylinder adapters 30 are placed in respective recesses 23 of injection head 21. If cylinder adapters 30 are placed in respective recesses 23, then cylinders 11 of normal syringes 10 which have a size corresponding to the size of recesses 32 in cylinder adapters 30 are placed in cylinder adapters 30.

In addition to normal syringes 10 described above, there is also available another liquid syringe which comprises rodless syringe 40 as shown in FIGS. 3a and 3b of the accompanying drawings. Rodless syringe 40 has piston 41 comprising a piston head free of a piston rod and having small-diameter piston flange 42 directly formed on an end of the piston head.

Generally, piston flanges 18 of normal syringes 10 are of a larger diameter than the inside diameter of cylinders 11. Piston pressers 26 of liquid injector 20 for holding piston flanges 18 of normal syringes 10 are also of a larger diameter than the inside diameter of cylinders 11.

Therefore, piston pressers 26 of liquid injector 20 cannot enter into cylinder 11 of rodless syringe 40, and hence are unable to directly press piston 41 of rodless syringe 40.

If rodless syringe 40 is mounted on liquid injector 20, then piston 41 thereof is connected to piston actuating mechanism 22 by piston adapter 50.

Piston adapter 50 has adapter rod 51 which is of the same shape as the shape of pistons 12 of normal syringes 10. Piston adapter 50 also has adapter flange 52 disposed on an end of adapter rod 51 and having the same shape as piston flange 18.

Adapter rod 51 of piston adapter 50 has cavity 53 defined in a distal end thereof for receiving piston flange 42 of rodless syringe 40. Flange holder 54 for openably closing cavity 53 is pivotably mounted on adapter rod 51.

The liquid injection system thus constructed operates as follows: Normal syringes 10 of the maximum size are directly mounted on injection head 21. Normal syringes 10 of other sizes than the maximum size are mounted on injection head 21 by respective dedicated cylinder adapters 30. Rodless syringes 10 are mounted on injection head 21 by respective dedicated piston adapters 50 and, if necessary, cylinder adapters 30.

If rodless syringes 10 are used, then flange holders 54 of piston adapters 50 are manually opened, piston flanges 42 are inserted into cavities 53, and thereafter flange holders 54 are manually closed.

Rodless syringes 40 with piston adapters 50 integrally coupled to pistons 41 have an outer shape identical to normal syringes 10. Therefore, rodless syringes 40 can be installed in injection head 21 of liquid injector 20, using cylinder adapters 30, if necessary, in the same manner as with normal syringes 10.

Cylinder 11 of rodless syringe 40 is held in recess 23 of injection head 21 by cylinder adapter 30, and adapter flange 52 of piston adapter 50 that is coupled to piston 41 is held by piston actuating mechanism 22.

Cylinder 11 is connected to the patient by an extension tube (not shown), and piston actuating mechanism 22 is operated to press piston adapter 50. Piston 41 is now pressed, together with piston adapter 50, into cylinder 11, injecting the liquid from cylinder 11 into the patient.

Normal syringes 10 and rodless syringes 40 are available in different types, i.e., a prefilled type wherein the syringe that has been filled with the liquid is shipped and used only once, and a refill type wherein the syringe is filled with the liquid by the operator for repetitive use.

With prefilled-type liquid syringes 10, 40, after pistons 12, 41 are pressed into cylinders 11 for injecting the liquid, there is no need to pull out pistons 12, 41.

Therefore, prefilled-type liquid syringes 10, 40 often have such a structure which makes it easy to press pistons 12, 41 into cylinders 11, but difficult to pull pistons 12, 41 out of cylinders 11.

The liquid injector described above has been invented and applied for patent by the applicant of the present application (see, for example, patent documents 1, 2). The piston adapter described above has been used by the applicant of the present application, but any known documents showing the piston adapter have not been found.

Patent document 1: Japanese laid-open patent publication No. 2002-11096.

Patent document 2: Japanese laid-open patent publication No. 2002-102343.

Liquid injector 20 is capable of injecting the liquid from normal syringe 10 into the patient, and is also capable of using rodless syringe 40 by combining it with piston adapter 50.

Piston adapter 50 has flange holder 54 on the tip end of piston rod 51 for releasably holding piston flange 42. Therefore, when piton rod 51 moves into cylinder 11 of rodless syringe 40 for injecting the liquid from cylinder 11 into the patient, flange holder 54 is no longer accessible for manual operation.

If rodless syringe 40 is of the prefilled type, then since piston 41 pressed into cylinder 11 is not pulled out, piston adapter 50 is not removed from rodless syringe 40 after the injection of the liquid has been completed. Consequently, it is the current practice to throw away piston adapter 50 together with rodless syringe 40 after use.

It would be possible to remove piston adapter 50 from rodless syringe 40 by detaching the extension tube which has connected the patient and rodless syringe 40 to each other, and pulling out piston adapter 50 together with piston 41 to the end of cylinder 11.

However, as described above, though it is easy to press piston 41 into cylinder 11 of prefilled-type rodless syringe 40, it is often difficult to pull piston 41 out of cylinder 11. Actually, therefore, it is hard to remove piston adapter 50 from rodless syringe 40, and even if piston 41 can easily be pulled out of cylinder 11, the process of removing piston adapter 50 from rodless syringe 40 is tedious and time-consuming.

In addition, the need for manually opening and closing flange holder 54 to release and hold piston flange 42 makes piston adapter 50 awkward to handle.

SUMMARY OF THE INVENTION

It is therefore an object of the present invention to provide a liquid injection system which allows a piston adapter to be removed from a piston easily after the piston adapter has been coupled to the piston of a rodless syringe and inserted into a cylinder.

According to a first aspect of the present invention, there is provided a liquid injection system having a normal syringe, a liquid injector, a rodless syringe, and a piston adapter. The piston adapter has an adapter rod, a flange holding mechanism, a manual operating member, and an interlink mechanism. The normal syringe has a slender cylinder having an opening defined in an end thereof and a piston having a slender piston rod with a piston head mounted on an end thereof and a piston flange disposed on the outer circumferential edge of an opposite end thereof, the piston being slidably inserted in the cylinder through the opening. The liquid injector has a piston actuating mechanism for holding and sliding the piston flange of the normal syringe. The rodless syringe has a slender cylinder having an opening defined in an end thereof and a piston having a piston head free of a piston rod and having a piston flange directly formed on an end of the piston head, the piston being slidably inserted in the cylinder through the opening. The piston adapter is of a slender shape and interconnects the piston flange of the rodless syringe and the piston actuating mechanism of the liquid injector.

The adapter rod is of a slender shape having an adapter flange for being held by the piston actuating mechanism, the adapter flange being disposed on the outer circumferential edge of an end of the adapter rod. The flange holding mechanism is mounted on an opposite end of the adapter rod for releasably holding the piston flange of the rodless syringe. The manual operating member is disposed on the adapter rod near the end thereof for being manually operated. The interlink mechanism at least releases the flange holding mechanism from the piston flange in conjunction with manual operation of the manual operating member.

With the liquid injection system according to the first aspect of the present invention, when the manual operating member near the end of the piston adapter is manually operated, the flange holding mechanism on the opposite end of the piston adapter is at least released. After the piston adapter is mounted on the piston of the rodless syringe and inserted into the cylinder thereof, the flange holding mechanism can be released from the piston in the cylinder by manually operating the manual operating member which is exposed from the cylinder. Even when the piston adapter is used on a prefilled-type rodless syringe where the piston can easily be pressed into the cylinder, but is difficult to pull out, the piston adapter can easily be removed from the rodless syringe for repetitive use.

According to a second aspect of the present invention, a piston adapter of a liquid injection system has an adapter rod, at least one engaging claw, and a closing mechanism. The engaging claw is openably and closably supported on an opposite end of the adapter rod for releasably holding the piston flange of the rodless syringe. The closing mechanism normally biases the engaging claw in a closing direction. When the piston adapter is pressed against the piston, the piston flange is automatically held by the engaging claw.

With the liquid injection system according to the second aspect of the present invention, since the engaging claw which is openably and closably supported on an opposite end of the adapter rod is normally biased in the closing direction, the piston adapter can simply and intuitively be mounted on the piston without the need for any special manual procedure.

According to a third aspect of the present invention, a piston adapter of a liquid injection system has an adapter rod and a flange holding mechanism. The flange holding mechanism is disposed on an opposite end of the adapter rod and angularly movable about its own axis for releasably holding the piston flange of the rodless syringe. After the piston adapter is mounted on the piston of the rodless syringe and inserted into the cylinder thereof, the flange holding mechanism can be released from the piston in the cylinder by turning the end of the piston adapter which is exposed from the cylinder.

With the liquid injection system according to the third aspect of the present invention, the flange holding mechanism disposed on the opposite end of the adapter rod disengageably engages the piston flange when the flange holding mechanism is turned about its own axis. After the piston adapter is mounted on the piston of the rodless syringe and inserted into the cylinder thereof, the flange holding mechanism can be released from the piston in the cylinder by turning the end of the piston adapter which is exposed from the cylinder. Consequently, even when the piston adapter is used on a prefilled-type rodless syringe where the piston can easily be pressed into the cylinder, but is difficult to pull out, the piston adapter can easily be removed from the rodless syringe for repetitive use.

Various components referred to in the present invention do not need to be a separate entity. Rather, those components may be constructed as one component, a certain component may be part of another component, or a certain component may have a portion overlapping a portion of another component.

The above and other objects, features, and advantages of the present invention will become apparent from the following description with reference to the accompanying drawings which illustrate examples of the present invention.

BRIEF DESCRIPTION OF THE DRAWINGS

FIGS. 4a and 4b are sectional plan views showing an internal structure of a piston adapter of a liquid injection system according to a first embodiment of the present invention;

FIGS. 8a and 8b are perspective views of an injection head of the liquid injector and a normal syringe;

DETAILED DESCRIPTION OF THE PREFERRED EMBODIMENTS

Structure of 1st Embodiment

Figure 1:
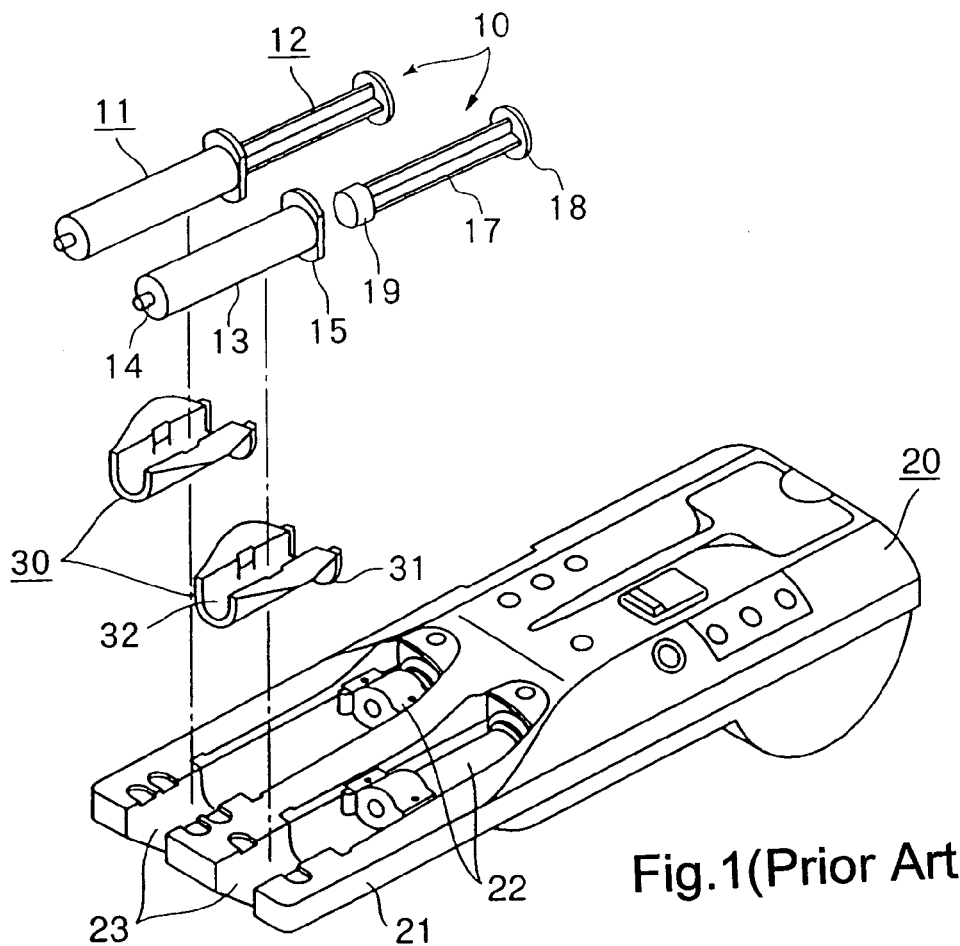
FIG. 1 is a perspective view of an injection head of a conventional liquid injector and normal syringes.
Figure 2:
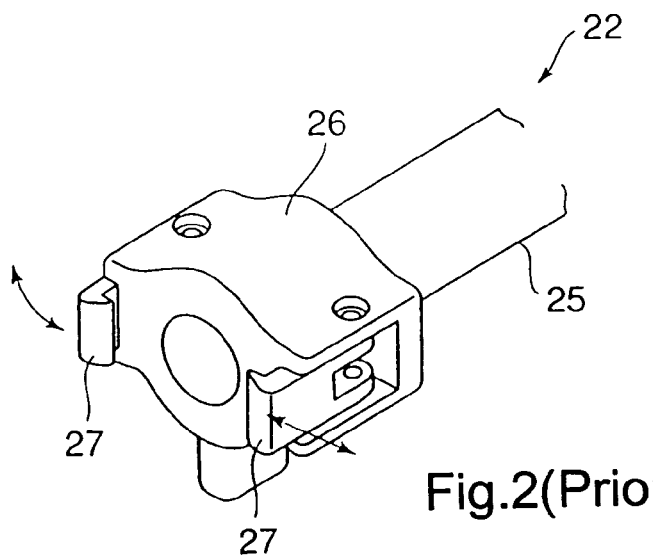
FIG. 2 is a fragmentary perspective view of a piston actuating mechanism of the conventional liquid injector shown in FIG. 1.
Figure 3A:
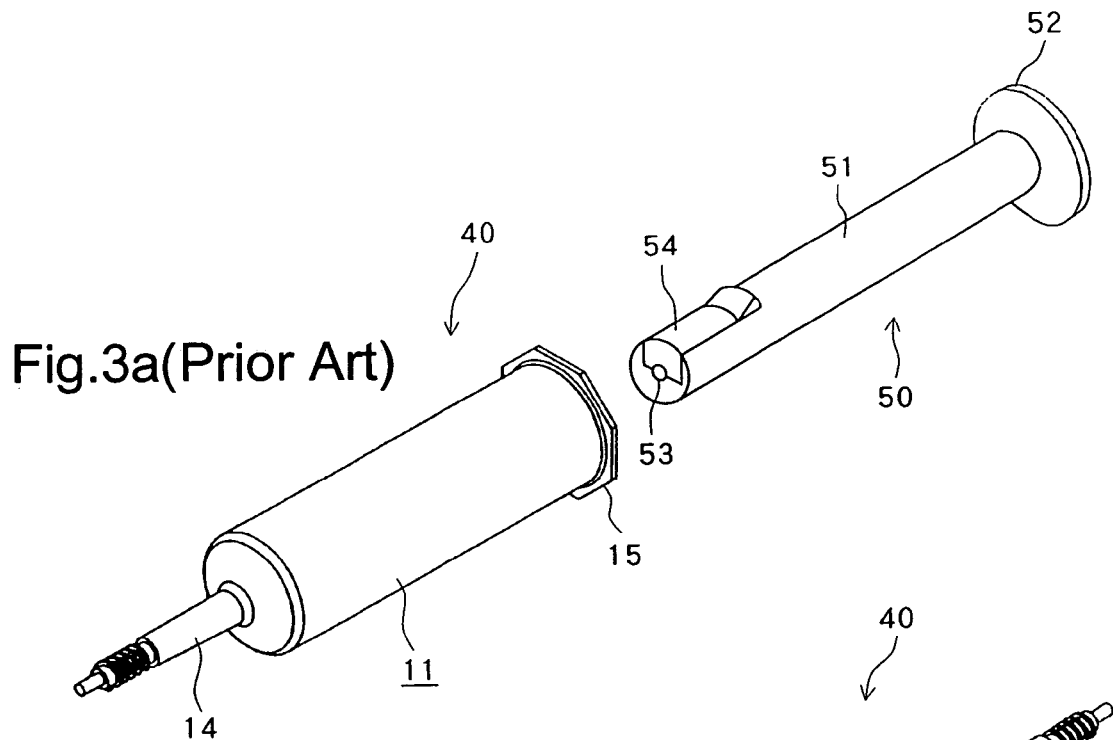
FIGS. 3a and 3b are perspective views of a piston adapter and a rodless syringe.
Figure 3B:
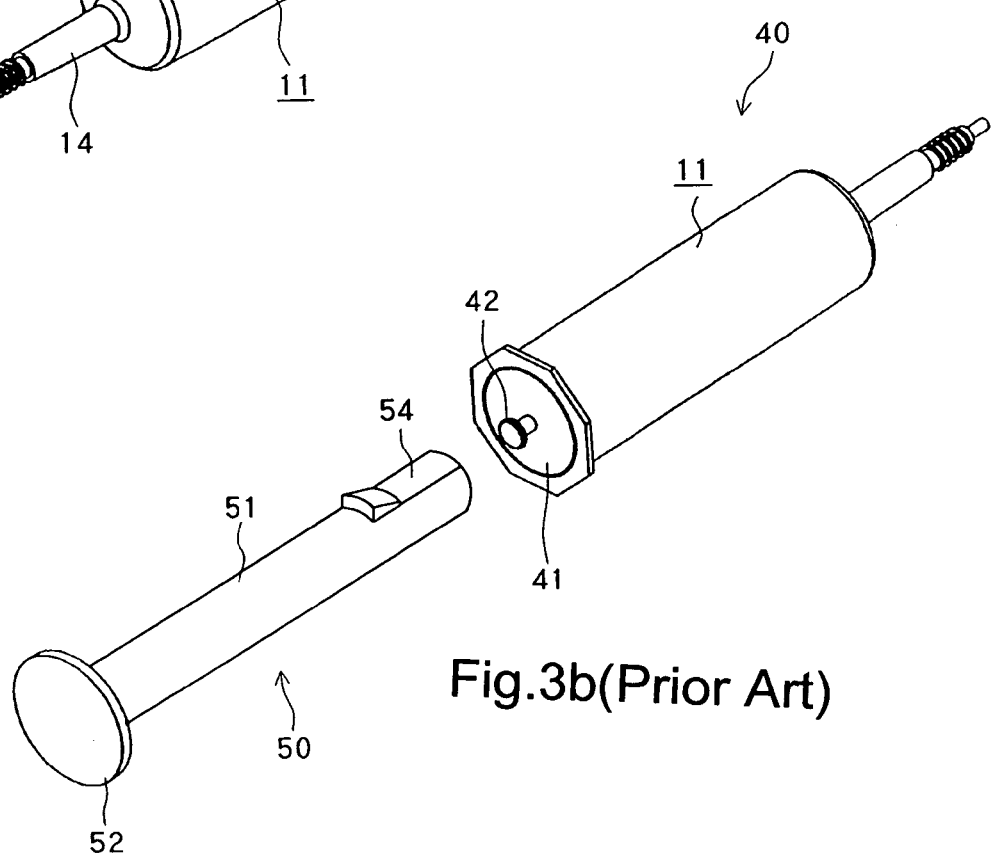
Figure 5:
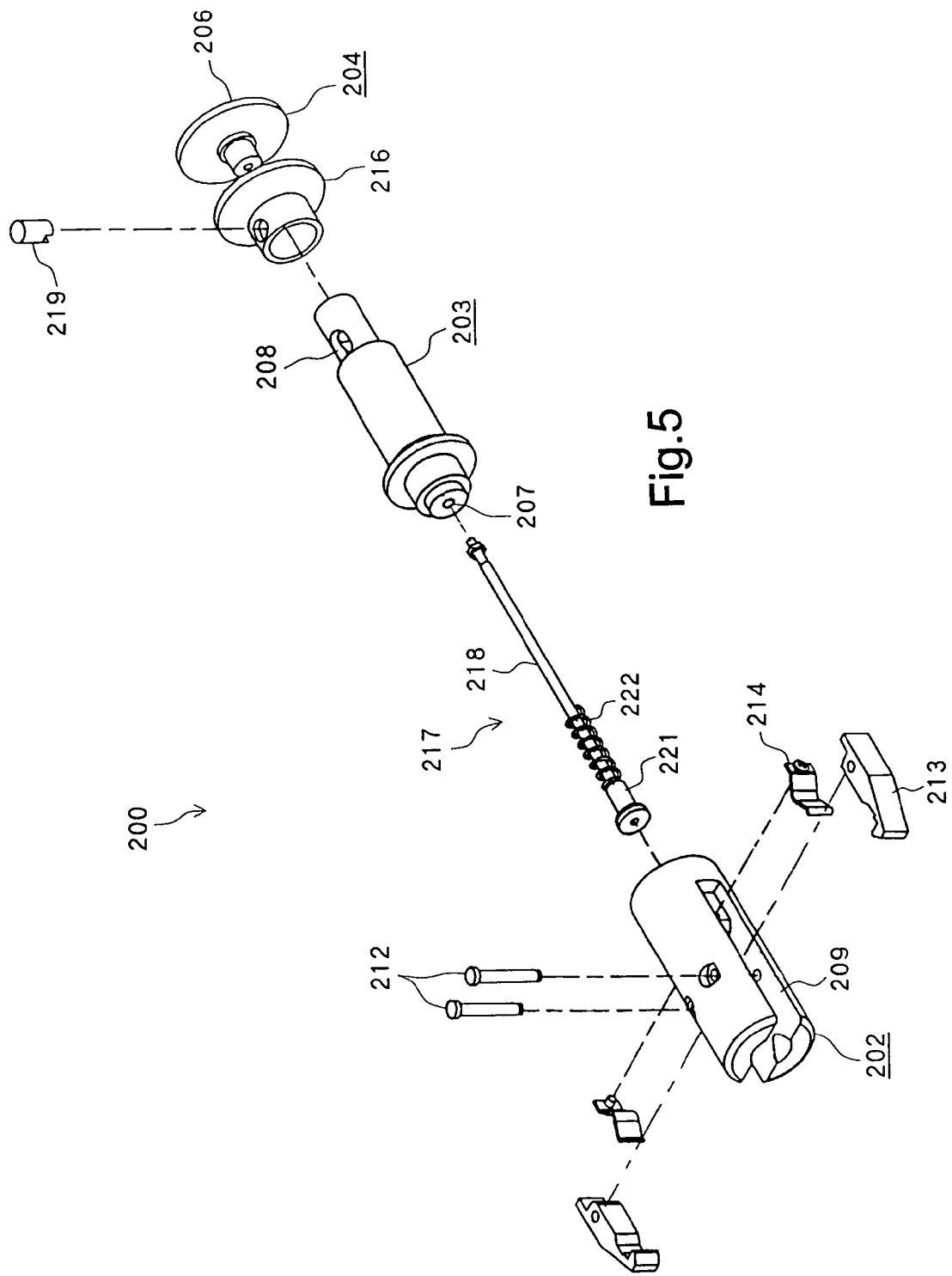
FIG. 5 is an exploded perspective view of the piston adapter shown in FIGS. 4a and 4b.

A liquid injection system according to a first embodiment of the present invention will be described below with reference to FIGS. 4a, 4b through 10. Those parts of the liquid injection system according to the first embodiment which are identical to those of the conventional liquid injection system are denoted by identical names and reference characters, and will not be described in detail below.

Certain terms with respect to forward, rearward, upward, downward, leftward, and rightward directions which will be referred to in the description are used for convenience only to simplify the illustration of relative positional relationships of various parts, and should not be interpreted as being limited to directions that are involved when the liquid injection system is manufactured and used.

Figure 10:
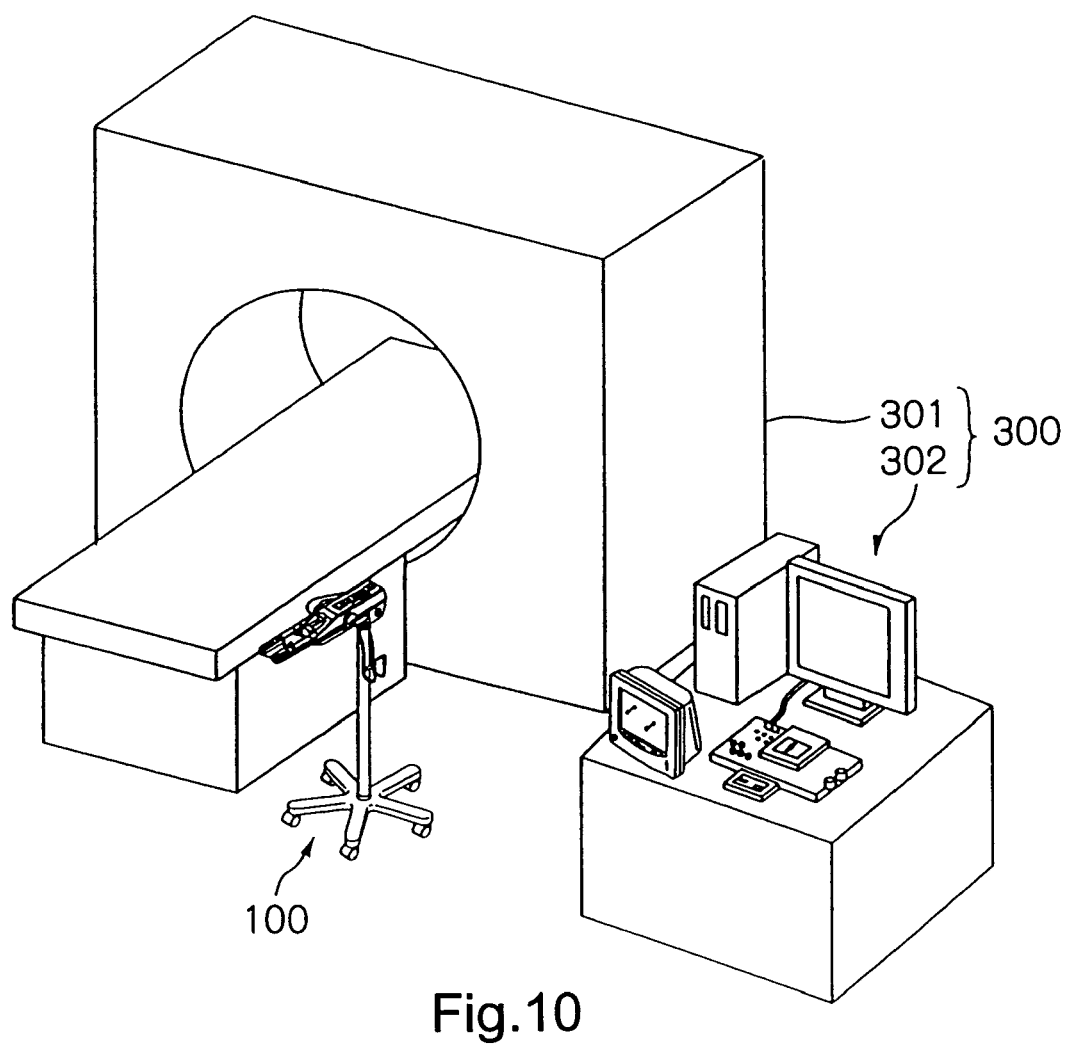
FIG. 10 is a perspective view of an MRI apparatus serving as an imaging diagnostic apparatus.

The liquid injection system according to the first embodiment has liquid injector 100, normal syringe 10, rodless syringe 40, piston adapter 200, etc. As shown in FIG. 10, the liquid injection system is used to inject a contrast medium into a patient when a fluoroscopic image of the patient is captured by MRI apparatus 300, for example.

MRI apparatus 300 comprises imaging unit 301 for capturing a tomographic image of the patient, and control unit 302 for controlling operation of imaging unit 301 and displaying a captured tomographic image of the patient.

Figure 9:
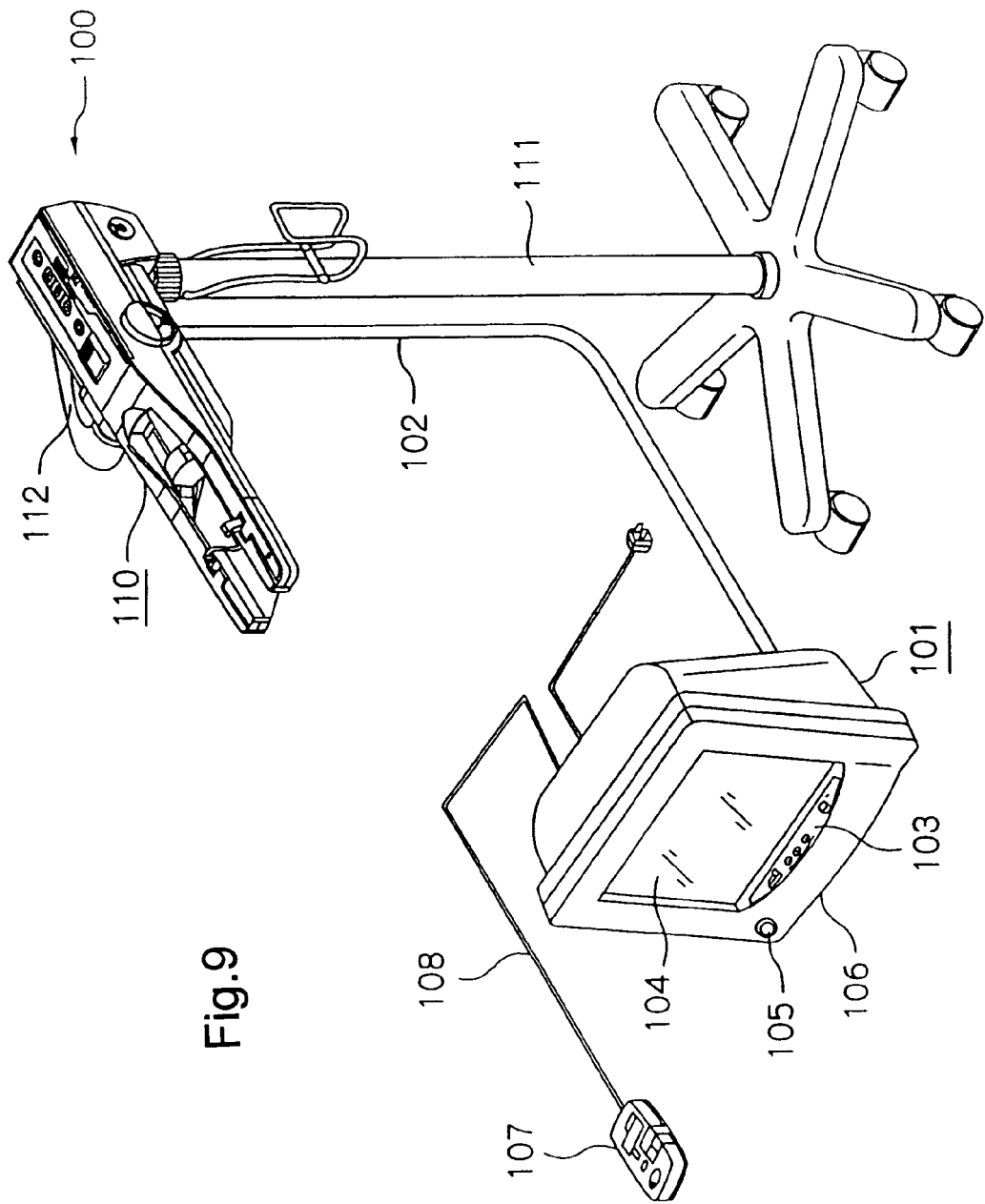
FIG. 9 is a perspective view of the liquid injector.

As shown in FIG. 9, liquid injector 100 comprises main injector unit 101 and injection head 110 which are connected to each other by communication cable 102. Injection head 110 actuates normal syringe 10 mounted thereon to inject a liquid into the patient, and main injector unit 101 controls operation of injection head 110.

Main injector unit 101 has console panel 103, touch panel 104 as a display panel, and speaker unit 105 which are disposed on the front face of a unit housing 106. Separate controller unit 107 is connected to main injector unit 101 by connector 108.

Main injector unit 101 houses therein a computer unit (not shown) and is connected to control unit 302 of MRI apparatus 300 by a communication network (not shown).

Injection head 110 is mounted on the upper end of caster stand 111 by movable arm 112. As shown in FIGS. 8a and 8b, injection head 110 includes head body 113 having semicylindrical groove-like recess 23 defined in an upper surface thereof for receiving normal syringe 10 removably mounted therein.

Injection head 110 has cylinder holding mechanism 116 positioned forwardly of recess 23 for holding cylinder flange 15 of normal syringe 10, and piston actuating mechanism 22 disposed rearwardly of recess 23 for holding and sliding piston flange 18 of normal syringe 10.

Piston actuating mechanism 22 has a drive motor (not shown) as a drive source. The drive motor comprises an ultrasonic motor made of a nonmagnetic material such as phosphor bronze alloy (Cu+Sn+P), titanium alloy (Ti–6Al–4V), magnesium alloy (Mg+Al+Zn), or the like. In operation, the ultrasonic motor does not produce magnetic forces which would otherwise affect the magnetic field of the imaging diagnostic apparatus.

As shown in FIGS. 4a, 4b through 6a, 6b, piston adapter 200 has slender adapter rod 201 comprising distal-end member 202, intermediate member 203, and terminal-end member 204 with adapter flange 206 disposed on the outer circumferential edge of the tip end of adapter rod 201.

Intermediate member 203 of adapter rod 201 has longitudinally through hole 207 defined centrally therein and elliptical hole 208 defined perpendicularly to an end of through hole 207. Distal-end member 202 also has longitudinally through opening 209 defined therein which has a slit end.

Flange holding mechanism 211 is incorporated in distal-end member 202 of adapter rod 201 for releasably holding piston flange 42 of rodless cylinder 40.

Specifically, flange holding mechanism 211 comprises a pair of engaging claws 213 openably and closably supported in distal-end member 202 by respective support shafts 212, and a pair of leaf springs 214 serving as a closing mechanism for normally biasing engaging claws 213 to move in a closing direction, i.e., to move toward each other. Engaging claws 213 which are openable and closable, i.e., movable toward and away from each other, and are normally biased in the closing direction, releasably hold piston flange 42 of rodless cylinder 40.

Manual operating member 216 which is similar in shape to adapter flange 206 is mounted on adapter rod 201 near the tip end thereof. Manual operating member 216 is supported on adapter rod 201 for sliding movement between a position where manual operating member 216 is held against adapter flange 206 and a position where manual operating member 216 is spaced from adapter flange 206.

Manual operating member 216 and flange holding mechanism 211 are coupled to each other by interlink mechanism 217 which has slender open interlocking mechanism 218 slidably disposed in opening 209 and through hole 207 of adapter rod 201.

Open interlocking mechanism 218 has a tip end positioned near the tip end of adapter rod 201. The tip end of open interlocking mechanism 218 and manual operating member 216 are coupled to each other by a joint 219 that is disposed in elliptical hole 208 of adapter rod 201.

Open interlocking mechanism 218 has wedge-shaped member 221 disposed on the distal end thereof, and wedge-shaped member 221 engages with confronting inner surfaces of a pair of engaging claws 213 at the tip sides of the pivotal point.

Coil spring 222 serving as a biasing mechanism is disposed around open interlocking mechanism 218. Coil spring 222 has an end held against the rear surface of wedge-shaped member 221 of open interlocking mechanism 218 and an opposite end held against the front surface of the rear end of opening 209 of adapter rod 201. Coil spring 222 normally biases open interlocking mechanism 218 to move toward the distal end of adapter rod 201.

The components of piston adapter 200 are made of various materials. These materials are nonmagnetic materials such as phosphor bronze alloy (Cu+Sn+P), titanium alloy (Ti–6Al–4V), magnesium alloy (Mg+Al+Zn), engineering plastic, FRP (Fiber-Reinforced Plastic), etc.

Figure 7A:
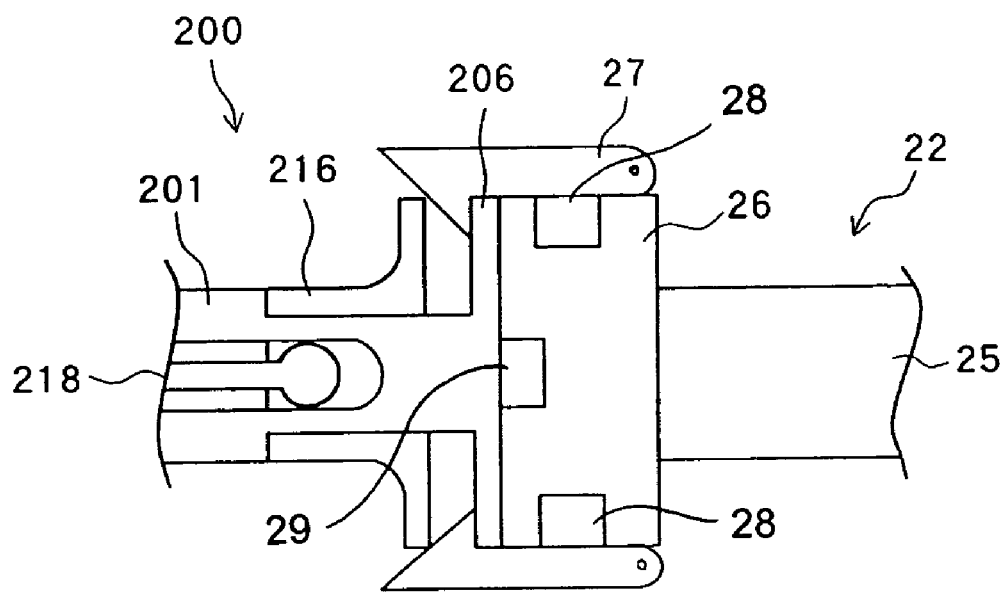
FIGS. 7a and 7b are fragmentary sectional plan views showing the manner in which a piston actuating mechanism of a liquid injector holds an adapter flange.
Figure 7B:
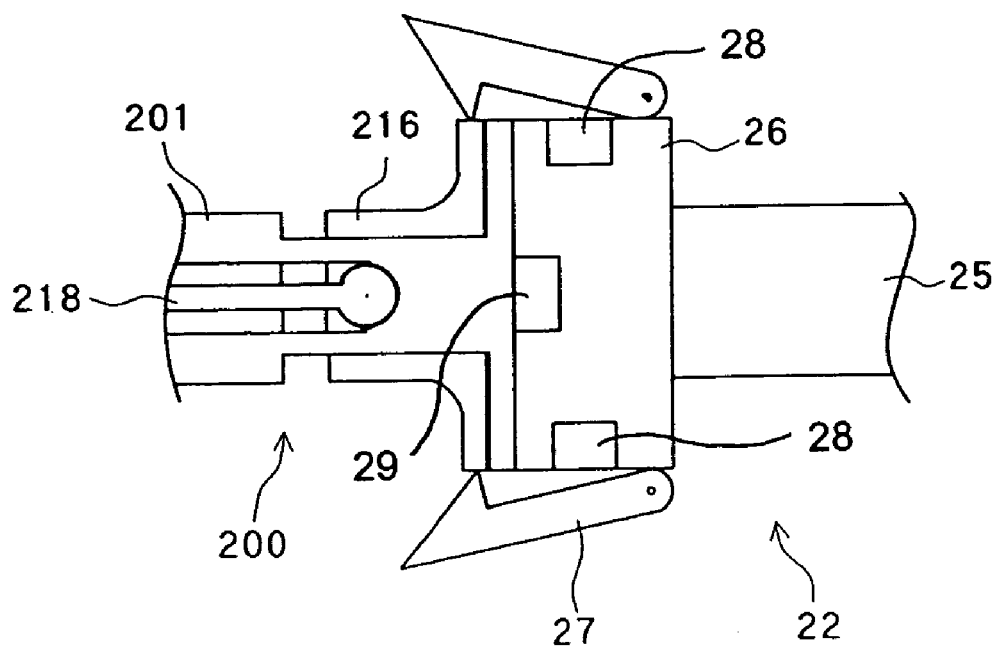

As shown in FIG. 7a, when manual operating member 216 of piston adapter 200 is spaced from adapter flange 206, adapter flange 206 is held by engaging teeth 27 of piston actuating mechanism 22 of liquid injector 100. However, as shown in FIG. 7b, when manual operating member 216 is held against adapter flange 206, adapter flange 206 is not held by engaging teeth 27 of piston actuating mechanism 22.

Opening/closing detecting sensors 28 for detecting when engaging teeth 27 are opened or closed are embedded in side faces of piston presser 26 of liquid injector 100. Abutment detecting sensor 29 for detecting whether adapter flange 206 abuts against piston presser 26 or not is embedded in a front face of piston presser 26.

These detecting sensors 28, 29 are connected to an operation control circuit (not shown) of liquid injector 100. The operation control circuit controls operation of piston actuating mechanism 22.

The operation control circuit comprises a microcomputer with a suitable computer program installed therein. As shown in FIG. 7a, when opening/closing detecting sensors 28 detect the closing of engaging teeth 27 and abutment detecting sensor 29 detects the abutment of adapter flange 206 against piston presser 26, the operation control circuit judges that adapter flange 206 is properly held by piston actuating mechanism 22, and makes piston actuating mechanism 22 operable.

As shown in FIG. 7b, when abutment detecting sensor 29 detects the abutment of adapter flange 206 against piston presser 26 and opening/closing detecting sensors 28 detect the opening of engaging teeth 27, the operation control circuit judges that adapter flange 206 is not properly held by piston actuating mechanism 22, and makes piston actuating mechanism 22 inoperable.

When opening/closing detecting sensors 28 detect the closing of engaging teeth 27 and abutment detecting sensor 29 does not detect (not shown) the abutment of adapter flange 206, the operation control circuit judges that adapter flange 206 is spaced from piston actuating mechanism 22, and makes piston actuating mechanism 22 operable until abutment detecting sensor 29 detects the abutment of adapter flange 206 against piston presser 26.

Operation of 1st Embodiment

The liquid injection system according to the first embodiment operates as follows: When normal syringe 11 of the maximum size is to be used, cylinder adapter 30 is not attached to liquid injector 100. When normal syringe 11 of a size other than the maximum size is to be used, cylinder adapter 30 is installed in liquid injector 100 as shown in FIGS. 8a and 8b.

When rodless syringe 40 is to be used, piston adapter 200 is mounted on piston 41 thereof, and if necessary, cylinder adapter 30 is installed in liquid injector 100. A process of using rodless syringe 40 will be described in detail below.

Figure 6A:
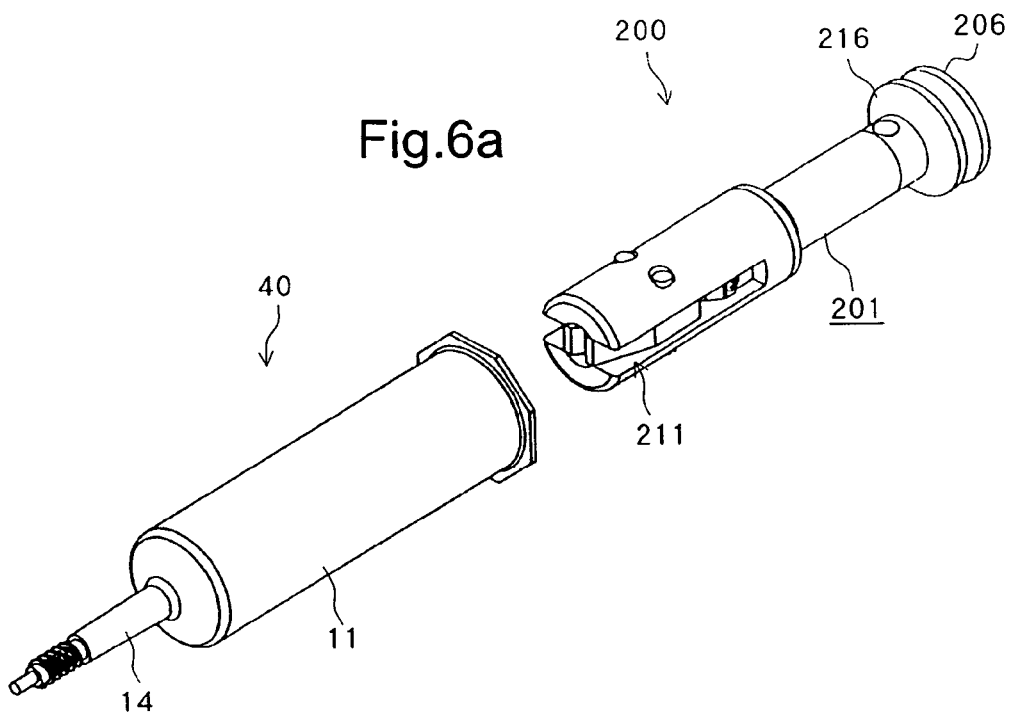
FIGS. 6a and 6b are perspective views of a piston adapter and a rodless syringe.
Figure 6B:
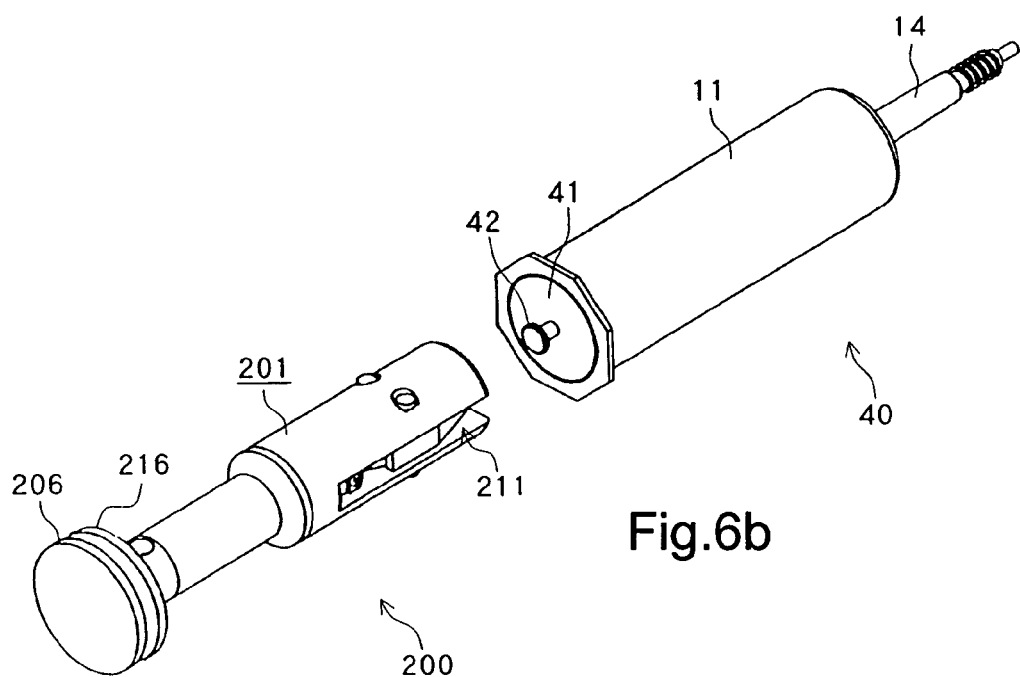

As shown in FIG. 6b, rodless cylinder 40 filled with a liquid is prepared, and flange holding mechanism 211 of piston adapter 200 is pressed against piston flange 42 of piston 41 that is positioned at the end of cylinder 11 of rodless cylinder 40.

Engaging claws 213 resiliently closed by leaf springs 214 are now spread away from each other by piston flange 42. As engaging claws 213 move further toward piston 41, engaging claws 213 snap back, holding piston flange 42 under the resiliency of leaf springs 214, as shown in FIG. 4a.

Since piston adapter 200 is securely coupled to cylinder 11, rodless syringe 40 can now be mounted on liquid injector 100, as is the case with normal syringe 10.

Conduit 14 of rodless syringe 40 is connected to a blood vessel of the patient by an extension tube (not shown), and then rodless syringe 40 is placed in recess 23 of injection head 110, using cylinder adapter 30 if necessary.

At this time, piston presser 26 of piston actuating mechanism 22 is initially located in a rearmost position. When the operator instructs console panel 103 of liquid injector 100 to hold the adapter flange, piston presser 26 is moved forwardly into abutment against piston adapter 200, whereupon engaging teeth 27 grip adapter flange 206.

At this time, opening/closing detecting sensors 28 detect the closing of engaging teeth 27, but abutment detecting sensor 29 does not detect the abutment of adapter flange 206 against piston presser 26. The operation control circuit judges that adapter flange 206 is spaced from piston actuating mechanism 22, and hence operates piston actuating mechanism 22 until abutment detecting sensor 29 detects the abutment of adapter flange 206 against piston presser 26.

If manual operating member 216 is held against adapter flange 206 of piston adapter 200, as shown in FIG. 7b, then engaging teeth 27 do not hold piston flange 206 even though piston presser 26 is held against piston adapter 200.

In this case, abutment detecting sensor 29 detects the abutment of adapter flange 206 against piston presser 26 and opening/closing detecting sensors 28 detect the opening of engaging teeth 27. Therefore, the operation control circuit judges that adapter flange 206 is not properly held by piston actuating mechanism 22.

The operation control circuit now makes piston actuating mechanism 22 inoperable. Consequently, even if the operator instructs console panel 103 to start injecting the liquid into the patient, piston actuating mechanism 22 does not press adapter flange 206.

The operation control circuit displays a warning guidance message, e.g., "SYRINGE NOT HELD, CONFIRM SYRINGE HOLDER", on touch panel 104. The operator then confirms engaging teeth 27 of piston actuating mechanism 22, and takes a suitable countermeasure.

In a normal situation where adapter flange 206 of piston adapter 200 is spaced from manual operating member 216, as shown in FIG. 7a, when piston presser 26 is held against piston adapter 200, engaging teeth 27 hold piston flange 206.

In this case, opening/closing detecting sensors 28 detect the closing of engaging teeth 27 and abutment detecting sensor 29 detects the abutment of adapter flange 206 against piston presser 26. The operation control circuit judges that adapter flange 206 is properly held by piston actuating mechanism 22.

The operation control circuit now makes piston actuating mechanism 22 operable. When the operator instructs console panel 103 to start injecting the liquid into the patient, piston actuating mechanism 22 presses adapter flange 206, injecting the liquid from cylinder 11 into the patient.

If rodless syringe 40 is of the prefilled type, then it is used only once to inject the liquid from cylinder 11. After piston 41 is pressed into cylinder 11, piston 41 is not pulled out of cylinder 11.

Therefore, prefilled-type rodless syringe 40 is generally of such a structure which makes it easy to press piston 41 into cylinder 11, but difficult to pull piston 41 out of cylinder 11.

When prefilled-type rodless syringe 40 is on liquid injector 100, the whole process is finished at the time piston 41 is pressed together with piston adapter 200 into cylinder 11.

The operator then removes prefilled-type rodless syringe 40 together with piston adapter 200 from injection head 110, and manually slides manual operating member 216 on the tip end of piston adapter 200 that is exposed from cylinder 11 toward adapter flange 206.

As shown in FIG. 4b, wedge-shaped member 221 on the distal end of open interlocking mechanism 218 which slides in unison with manual operating member 216 spreads or opens engaging claws 213 away from piston flange 42, thus releasing piston adapter 200 from piston 41 within cylinder 11.

Advantages of 1st Embodiment

The liquid injection system according to the first embodiment allows rodless syringe 40 with piston adapter 200 mounted thereon to be installed in liquid injector 100, as is the case with normal syringe 10. Even when piston 41 and piston adapter 200 are pressed into cylinder 11 of rodless syringe 40, piston adapter 200 can be removed from piston 41 by manually moving manual operating member 216 which is exposed from cylinder 11.

Therefore, piston adapter 200 can easily be removed from rodless syringe 40 without the need for sliding piston 41 to the end of cylinder 11. Piston adapter 200 can thus repeatedly be used while rodless syringe 40 is thrown away once used.

With piston adapter 200 according to the present embodiment, since flange holding mechanism 211 for holding piston flange 42 comprises a pair of engaging claws 213 that are normally biased into the closed position under the resiliency of leaf springs 214, engaging claws 213 automatically hold piston flange 42 when piston adapter 200 is pressed against piston 41. Consequently, piston adapter 200 can simply and intuitively be mounted on piston 41 without the need for any special manual procedure.

Furthermore, engaging claws 213 release piston 41 when manual operating member 216 positioned near adapter flange 206 is manually slid toward adapter flange 206.

Therefore, when manual operating member 216 is gripped and piston adapter 200 is pulled from rodless syringe 40, piston adapter 200 can be released from rodless syringe 40. The process of releasing piston adapter 200 from rodless syringe 40 is thus simple and intuitive.

Liquid injector 100 according to the present embodiment is used in the vicinity of MRI apparatus 300. Since piston adapter 200 is made of a nonmagnetic material in its entirety, it does not adversely affect the magnetic field of MRI apparatus 300.

Similarly, since the drive motor of liquid injector 100 comprises an ultrasonic motor made of a nonmagnetic material, liquid injector 100 and piston adapter 200 can be used without any problems in the vicinity of MRI apparatus 300.

If piston adapter 200 does not hold piston flange 42 due to a failure of open interlocking mechanism 218, as shown in FIG. 4b, then piston adapter 200 is not gripped by piston actuating mechanism 22 of liquid injector 100, as shown in FIG. 7b.

As piston actuating mechanism 22 which does not grip piston adapter 200 remains inoperable, piston actuating mechanism 22 is automatically prevented from operating while piston adapter 200 is not holding piston flange 42.

Modifications of 1st Embodiment

The present invention is not limited to the above embodiment, but various changes and modifications may be made therein without departing from the scope of the invention.

For example, although it is assumed in the above embodiment that liquid injector 100 is used in the vicinity of MRI apparatus 300, liquid injector 100 may also be used in the vicinity of a CT scanner or an angiography apparatus.

In the above embodiment, piston adapter 200 has a pair of engaging claws 213. However, piston adapter 200 may have one or three or more engaging claws 213. It is nevertheless effective to use a pair of engaging claws 213 for holding piston flange 42 stably with a simple structure.

In the above embodiment, open interlocking mechanism 218 comprises a rigid body in its entirety. However, only wedge-shaped member 221 may comprise a rigid body and may be connected to manual operating member 216 by a flexible wire, and such an assembly may be used as an open interlocking mechanism (not shown).

In the above embodiment, manual operating member 216 of piston adapter 200 is of the same diameter as adapter flange 206. However, manual operating member 216 may be smaller or larger in diameter than adapter flange 206, or may be different in shape different from adapter flange 206.

In the above embodiment, injection head 110 has single recess 23 and single piston actuating mechanism 22. However, the present invention is also applicable to a liquid injector (not shown) having a plurality of recesses 23 and a plurality of piston actuating mechanisms 22 on the injection head.

Structure of 2nd Embodiment

Figure 11:
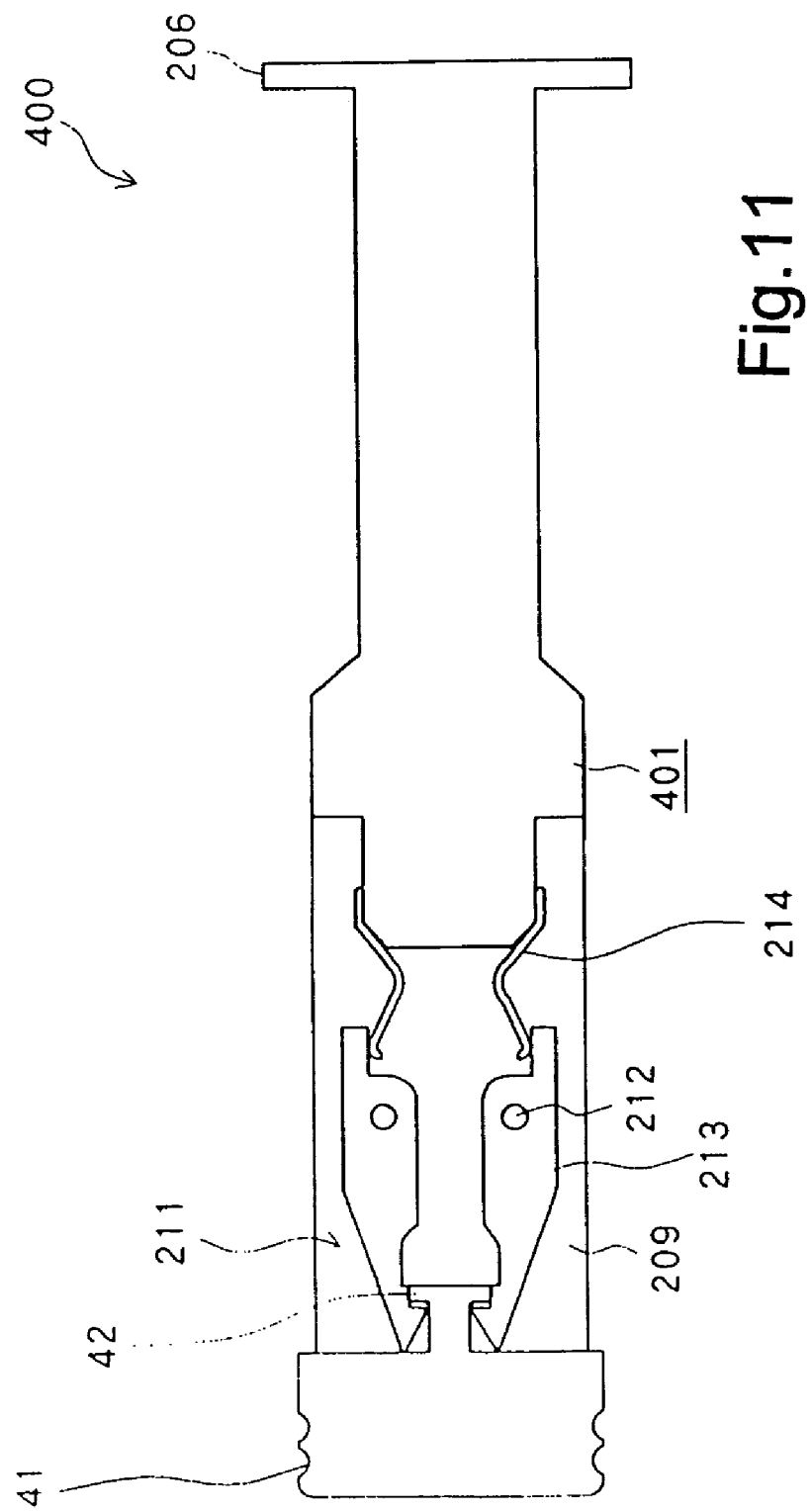
FIG. 11 is a sectional plan view showing an internal structure of a piston adapter of a liquid injection system according to a second embodiment of the present invention.

A liquid injection system according to a second embodiment of the present invention will be described below with reference to FIG. 11. The liquid injection system according to the second embodiment has piston adapter 400 including slender adapter rod 401. Flange holding mechanism 211 having engaging claws and leaf springs 214 is mounted on the distal end of slender adapter rod 401. However, piston adapter 400 is free of manual operating member 216 and interlink mechanism 217.

Operation of 2nd Embodiment

The liquid injection system according to the second embodiment operates as follows: When flange holding mechanism 211 on the distal end of piston adapter 400 is pressed against piston flange 42 of piston 41 that is positioned at the end of cylinder 11 of rodless cylinder 40, engaging claws 213 that are resiliently closed by leaf springs 214 are spread away from each other by piston flange 42. As engaging claws 213 move further toward piston 41, engaging claws 213 snap back, holding piston flange 42 under the resiliency of leaf springs 214.

Advantages of 2nd Embodiment

With piston adapter 400 according to the second embodiment, since flange holding mechanism 211 for holding piston flange 42 comprises a pair of engaging claws 213 that are normally biased into the closed position under the resiliency of leaf springs 214, engaging claws 213 automatically hold piston flange 42 when piston adapter 400 is pressed against piston 41. Consequently, piston adapter 400 can simply and intuitively be mounted on piston 41 without the need for any special manual procedure.

Structure of 3rd Embodiment

Figure 12:
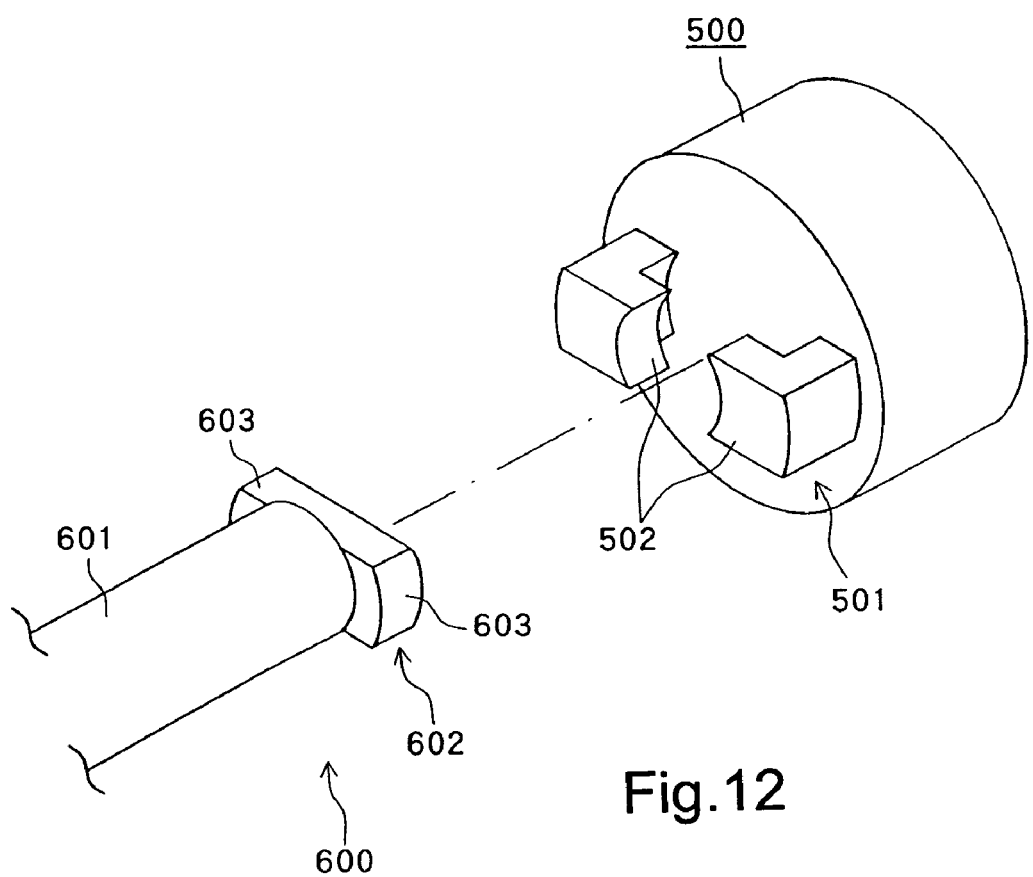
FIG. 12 is a fragmentary perspective view of a piston adapter and a piston of a liquid injection system according to a third embodiment of the present invention.

A liquid injection system according to a third embodiment of the present invention will be described below with reference to FIG. 12. The liquid injection system according to the third embodiment has a rodless syringe (not shown) having piston 500 including piston flange 501 which comprises a pair of engaging hooks 502 projecting radially inwardly toward each other, and piston adapter 600 including flange holding mechanism 602 mounted on the distal end of adapter rod 601. Flange holding mechanism 602 comprises a pair of holders 603 projecting radially outwardly away from each other.

Operation of 3rd Embodiment

The liquid injection system according to the third embodiment operates as follows: Engaging hooks 502 of piston 500 and holders 603 of piston adapter 600 are oriented perpendicularly to each other, i.e., the direction in which engaging hooks 502 project radially inwardly toward each other and the direction in which holders 603 project radially outwardly away from each other are oriented perpendicularly to each other. Then, piston adapter 600 is brought into abutment against piston 500 from behind to place holders 603 on the end of piston 500 past engaging hooks 502. Then, piston adapter 600 is turned 900 about its own axis to bring holders 603 into engagement with respective engagming hooks 502, whereupon piston adapter 600 is securely coupled to piston 500.

When piston adapter 600 is further turned 90° or turned back 90°, holders 603 are disengaged from respective engaging hooks 502. Now, piston adapter 600 is released from piston 500.

Advantages of 3rd Embodiment

When flange holding mechanism 602 on the distal end of adapter rod 601 is turned about its own axis, it is brought into and out of engagement with piston flange 501. After piston adapter 600 is mounted on piston 500 of the rodless syringe and inserted into the cylinder thereof, flange holding mechanism 602 can be released from piston 500 in the cylinder by turning the end of piston adapter 600 which is exposed from the cylinder.

Even if piston adapter 600 is used on a prefilled-type rodless syringe which makes it easy to press piston 500 into the cylinder, but difficult to pull piston 500 out of the cylinder, piston adapter 600 can easily be removed from the rodless syringe for repetitive use.

Modifications of 3rd Embodiment

In the above embodiment, piston flange 501 comprises a pair of engaging hooks 502 projecting radially inwardly toward each other, and flange holding mechanism 602 of piston adapter 600 comprises a pair of holders 603 projecting radially outwardly away from each other. However, a piston flange may comprise a plurality of engaging hooks projecting radially inwardly and a flange holding mechanism of a piston adapter may comprise a plurality of holders projecting radially outwardly.

While preferred embodiments of the present invention has been described using specific terms, such description is for illustrative purposes only, and it is to be understood that changes and variations may be made without departing from the spirit or scope of the following claims.

What is claimed is:

1. A liquid injection system, comprising:
a liquid injector having a piston actuating mechanism for holding and sliding a piston flange of a normal syringe;
a rodless syringe having a slender cylinder having an opening defined in an end thereof and a piston having a piston head free of a piston rod and having a piston flange directly formed on an end of the piston head, said piston being slidably inserted in said cylinder through said opening; and
a slender piston adapter for use with said rodless syringe instead of the normal syringe in said liquid injector and interconnecting the piston flange of said rodless syringe and said piston actuating mechanism of said liquid injector;

said piston adapter comprising:
a slender adapter rod having a first end and a second end, and an adapter flange for being held by said piston actuating mechanism, said adapter flange being disposed on an outer circumferential edge of the first end of the adapter rod;
a flange holding mechanism mounted on the second end of said adapter rod for releasably holding the piston flange of said rodless syringe, said flange holding mechanism comprises at least one engaging claw openably and closably supported on said adapter rod for releasably holding the piston flange of said rodless syringe and a closing mechanism for normally biasing said engaging claw in a closing direction;
a manual operating member disposed on said adapter rod near the first end thereof for being manually operated; and an interlink mechanism for at least releasing said flange holding mechanism from said piston flange in conjunction with manual operation of said manual operating member;

wherein said manual operating member is longitudinally slidably supported on said adapter rod, and said flange holding mechanism comprises a plurality of engaging claws, said interlink mechanism comprising:

a slender open interlocking mechanism having an end coupled to said manual operating member and a wedge-shaped member disposed on an opposite end thereof for spreading said engaging claws away from each other when said open interlocking mechanism is slid toward the first end of said adapter rod; and a biasing mechanism for normally biasing said open interlocking mechanism toward the second end of said adapter rod.

2. A liquid injection system according to claim 1, wherein said manual operating member is of a shape similar to said adapter flange and is supported for sliding movement between a position where the manual operating member is held against said adapter flange and a position where said manual operating member is spaced from said adapter flange;

said flange holding mechanism holds said piston flange when said manual operating member is in the position where said manual operating member is spaced from said adapter flange, and releases said piston flange when said manual operating member is in the position where said manual operating member is held against said adapter flange; and said piston actuating mechanism holds said adapter flange when said manual operating member is spaced from said adapter flange and does not hold said adapter flange when said manual operating member is held against said adapter flange.

3. A liquid injection system according to claim 2, wherein said liquid injector comprises:

holding detecting means for detecting whether said piston actuating mechanism holds said adapter flange or not; and operation control means for making said piston actuating mechanism inoperable if said piston actuating mechanism does not hold said adapter flange as detected by said holding detecting means.

4. A liquid injection system according to claim 1, wherein said piston adapter is made of a nonmagnetic material, and said piston actuating mechanism has an ultrasonic motor serving as a drive source and made of a nonmagnetic material.

5. A piston adapter for use with a rodless syringe instead of a normal syringe in a liquid injector comprising:

a slender adapter rod having a first end and a second end, and an adapter flange for being held by a piston actuating mechanism of said injector, said adapter flange being disposed on an outer circumferential edge of the first end of the adapter rod;

a flange holding mechanism mounted on the second end of said adapter rod for releasably holding a piston flange of said rodless syringe, said flange holding mechanism comprises at least one engaging claw openably and closably supported on said adapter rod for releasably holding the piston flange of said rodless syringe and a closing mechanism for normally biasing said engaging claw in a closing direction;

a manual operating member disposed on said adapter rod near the first end thereof for being manually operated; and an interlink mechanism for at least releasing said flange holding mechanism from said piston flange in conjunction with manual operation of said manual operating member, wherein said manual operating member is longitudinally slidably supported on said adapter rod, and said flange holding mechanism comprises a plurality of engaging claws, said interlink mechanism comprising:

a slender open interlocking mechanism having an end coupled to said manual operating member and a wedge-shaped member disposed on an opposite end thereof for spreading said engaging claws away from each other when said open interlocking mechanism is slid toward the first end of said adapter rod; and a biasing mechanism for normally biasing said open interlocking mechanism toward the second end of said adapter rod.

* * * * *